United States Patent
Sonderegger et al.

(10) Patent No.: US 9,062,337 B2
(45) Date of Patent: Jun. 23, 2015

(54) CELL CULTURE MEDIUM AND PROCESS FOR PROTEIN EXPRESSION, SAID MEDIUM AND PROCESS COMPRISING A PAM INHIBITOR

(75) Inventors: Corinna Sonderegger, Kundl (AT); Julia Schmutzhard, Kundl (AT); Christine Heel, Kundl (AT); Thomas Stangler, Kundl (AT)

(73) Assignee: Sandoz GmbH, Kundl, Tirol (AT)

( * ) Notice: Subject to any disclaimer, the term of this patent is extended or adjusted under 35 U.S.C. 154(b) by 0 days.

(21) Appl. No.: 13/883,986

(22) PCT Filed: Nov. 9, 2011

(86) PCT No.: PCT/EP2011/069756
§ 371 (c)(1), (2), (4) Date: May 22, 2013

(87) PCT Pub. No.: WO2012/062810
PCT Pub. Date: May 18, 2012

(65) Prior Publication Data
US 2013/0337506 A1    Dec. 19, 2013

(30) Foreign Application Priority Data
Nov. 9, 2010  (EP) .................................... 10190532

(51) Int. Cl.
C07K 16/00  (2006.01)
C12P 21/00  (2006.01)
C12N 5/00   (2006.01)

(52) U.S. Cl.
CPC ................. *C12P 21/00* (2013.01); *C07K 16/00* (2013.01); *C12N 5/0018* (2013.01); *C12N 2501/70* (2013.01)

(58) Field of Classification Search
None
See application file for complete search history.

(56) References Cited

FOREIGN PATENT DOCUMENTS

| | | |
|---|---|---|
| AU | 2011328166 | 11/2011 |
| CA | 2816394 | 11/2011 |
| CN | 201180053542.X | 11/2011 |
| EP | 10190532.1 | 11/2010 |
| EP | 11782121.5 | 11/2011 |
| IN | 4260/DELNP/2013 | 11/2011 |
| JP | 2013-538186 | 11/2011 |
| KR | 10-2013-7013920 | 11/2011 |
| SG | 201303487-1 | 11/2011 |
| WO | WO 2006/084111 | 8/2006 |
| WO | WO 2007/087253 | 8/2007 |
| WO | PCT/EP2011/069756 | 11/2011 |

OTHER PUBLICATIONS

Mains et al. "Inhibition of peptide amidation by disulfiram and diethyldithiocarbamate" 1986 Journal of Biochemistry 261 11938-11941.*
Takahashi et al "Production of bioactive salmon calcitonin from the nonendocrine cell ines COS-7 and CHO" 1997 Peptides 18: 439-444.*
Bradbury et al. "4-phenyl-3-butenoic acid an in vivo inhibitor of peptidylglycine hydroxylase" 1990 Eur J Biochem 189 363-368.*
Wang et al "Erythropoietin production form CHO cells grown by continuous culture in a fluidized bed bioreactor" 2002 Biotechnology and Bioengineering 77 194-203.*
Bauer JD, et al. (2007) Anti-inflammatory effects of 4-phenyl-3-butenoic acid and 5-(acetylamino)-4-oxo-6-phenyl-2-hexenoic acid methyl ester, potential inhibitors of neuropeptide bioactivation. J Pharmacol Exp Ther. 320(3): 1171-1177.
Chew G. (2003). Substrate-based inhibitors of pepitdylglycine Amidating Monooxygenase (PAM) as anti-proliferative drugs for cancer. University of South Florida—*Graduate School Theses and Dissertations*. (49 pages) Available at http://scholarcommons.usf.edu/etd/1341/.
Mains RE, et al. (1986) Inhibition of peptide amidation by disulfiram and diethyldithiocarbamate. J Biol Chem. 261(26): 11938-11941.
Sunman JA, et al. (2004) Reversal of the transformed phenotype and inhibition of peptidylglycine alpha-monooxygenase in Ras-transformed cells by 4-phenyl-3-butenoic acid. Mol Carcinog. 41(4): 231-246.
Iwai N, et al. (1999) Autocrine growth loops dependent on peptidyl alpha-amidating enzyme as targets for novel tumor cell growth inhibitors. Lung Cancer. 23(3): 209-222.
Walsh G, et al. (2006) Post-translational modifications in the context of therapeutic proteins. Nat Biotechnol. 24(10): 1241-1252.
International Search Report mailed May 21, 2012 for PCT/EP2011/069756 which was filed Nov. 1, 2011 and published on May 18, 2012 as WO 2012/062810 (Applicant—Sandoz GmbH // Inventors—Sonderegger et al.) (6 pages).
International Preliminary Report on Patentability mailed May 14, 2013 for PCT/EP2011/069756 which was filed Nov. 1, 2011 and published on May 18, 2012 as WO 2012/062810 (Applicant—Sandoz GmbH // Inventors—Sonderegger et al.) (12 pages).
Written Opinion mailed May 9, 2013 for PCT/EP2011/069756 which was filed Nov. 1, 2011 and published on May 18, 2012 as WO 2012/062810 (Applicant—Sandoz GmbH // Inventors—Sonderegger et al.) (11 pages).
Gumbiner, B. & Kelly R. B., "Two distinct intracellular pathways transport secretory and membrane glycoproteins to the surface of pituitary tumor cells," Jan. 1982, Cell, vol. 28, 51-59.

* cited by examiner

*Primary Examiner* — Suzanne M Noakes
*Assistant Examiner* — Gerard Lacourciere
(74) *Attorney, Agent, or Firm* — Ballard Spahr LLP

(57) ABSTRACT

The present invention is related to a cell culture medium for the expression of a protein, which medium comprises a PAM inhibitor, or a physiological equivalent thereof, and to a cell culture process for the expression of a protein, in which process a PAM inhibitor, or a physiological equivalent thereof, is used (FIG. 1).

13 Claims, 3 Drawing Sheets

Figure 1:
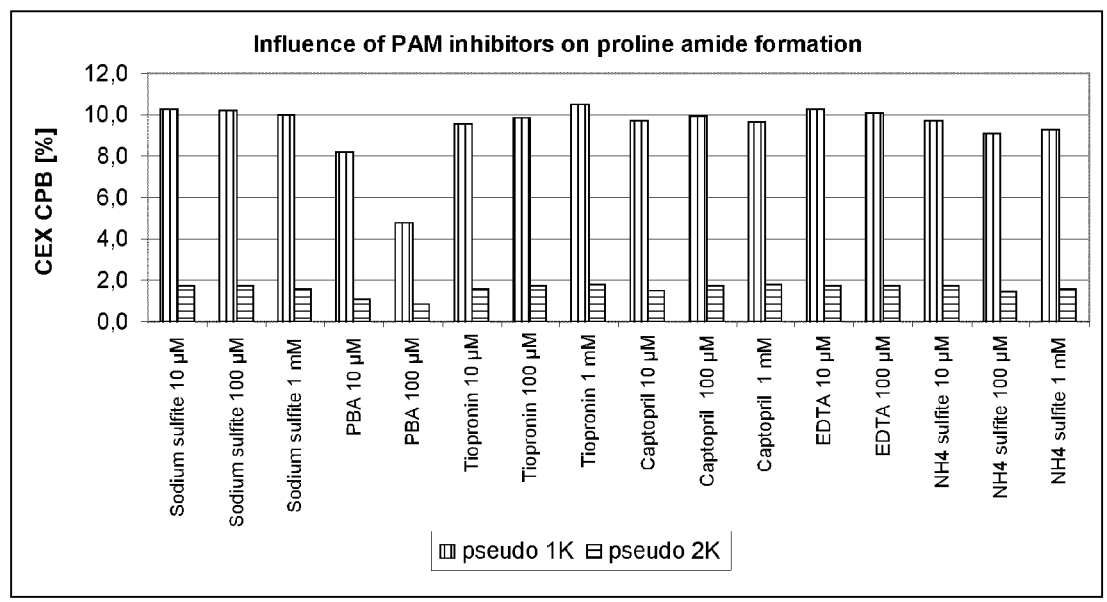

CELL CULTURE MEDIUM AND PROCESS FOR PROTEIN EXPRESSION, SAID MEDIUM AND PROCESS COMPRISING A PAM INHIBITOR

CROSS REFERENCE TO RELATED APPLICATIONS

The present application is a National Phase Application of International Application No. PCT/EP 2011/069756, filed Nov. 9, 2011, which claims priority to European Patent Application No. 10190532.1, filed Nov. 9, 2010, which applications are incorporated herein fully by this reference.

The present invention is related to a cell culture medium and process comprising a PAM inhibitor, or a physiological equivalent thereof.

Although proteins are mainly characterized by their amino acid sequence (primary structure), other aspects, like post-translational modifications, contribute to the characteristics of a protein as well, affecting secondary, tertiary and quartary structure. Some of these post-translational modifications play a significant role for later protein activity, including safety and efficacy of biopharmaceutical drugs.

One major aspect for the heterogeneity of proteins is the charge pattern including acidic variants, formed, for example, by deamidation of amino acids like asparagines, by glycation or by processing of N-terminal glutamine to pyroglutamate, and basic variants, with, for example, C-terminal lysine variants and amidated amino acids, particularly C-terminal proline amide residues.

The formation of C-terminal proline amide residues is however unwanted in some cases, e.g., as source of undesired heterogeneity, or in case said variants potentially affect protein activity or immunogenicity, or when the amount of amidated amino acids, e.g., proline amide, in the protein which is to be produced is higher, or lower, than in a reference protein.

In contrast to small molecular drugs, which are being produced under highly controllable physico-chemical conditions, the production of proteins, particularly proteins used as biotherapeutics, is a highly complex matter which is difficult to control, as the production makes use of a living cell culture system. Therefore, it is important to have at hand a toolbox which allows to control particularly post-translational modifications of the proteins produced, in order to be able to provide a constant product quality and a constantly high yield, to increase the efficiency of the production process, to increase and/or fine tune the physiological activity of the protein produced and the safety of the derived drug, and/or to match the post-translational features of a produced protein to those of a reference protein.

It is the object of the present invention to provide a process, and a medium for protein expression which addresses these needs.

These objects are met with methods and means according to the independent claims of the present invention. The dependent claims are related to preferred embodiments. It is to be understood that value ranges delimited by numerical values are to be understood to include the said delimiting values.

SUMMARY OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an", and "the" include singular and/or plural referents unless the context clearly dictates otherwise. It is moreover to be understood that, in case parameter ranges are given which are delimited by numeric values, the ranges are deemed to include these limitation values.

According to a first aspect of the present invention, a cell culture medium for the expression of a protein is provided, which medium comprises a PAM inhibitor, or a physiological equivalent thereof. According to another aspect of the invention, a cell culture process for the expression of a protein is provided, in which process a PAM inhibitor, or a physiological equivalent thereof, is used.

PAM (peptidylglycine alpha amidating monooxigenase) is a multifunctional protein containing two enzymatic activities that act sequentially to catalyze the C-terminal truncation and alpha-amidation of peptides. Peptidylglycine alpha-hydroxylating monooxygenase (PHM) catalyzes the first step of the reaction and is dependent on copper (Cu), or copper ions, ascorbate, and molecular oxygen. The zinc dependent peptidylamido-glycolate lyase (PAL) catalyzes the second step of the reaction, the amidation of the now C-terminal proline to proline amide.

PAM inhibitors are substances that lower the rate of catalysis of the PAM complex. Chew (2003) suggests that a PAM inhibitor could be useful as an anti-proliferative drug, while Bauer et al. (2007) suggest that some PAM inhibitors have anti-inflammatory effects. So far, however, the use of PAM inhibitors in cell culture media or processes, particularly in protein expression, more particularly in the expression of heterologous proteins, has not been described.

Some examples for PAM inhibitors are mentioned in the following list:
S-(Thiobenzoyl)thioglycolic acid
N-(Phenylthioacetyl)alanine
S-(4-Methylthiobenzoyl)thioglycolic acid
4-Cyano-4-methyl-4-thiobenzoyl-sulfanylbutyric acid
S-(4- Methylthiobenzoyl)thioglycolic acid ethyl ester
S-(N-Phenylthiocarbamoyl)-3-mercaptopropionic acid
S-(Phenylthioacetyl)thioglycolic acid
S-(N-Phenylthiocarbamoyl)thioglycolic acid
S-(3-Phenylthiopropionyl)thioglycolic acid
N-Glycolic Acid phenyl urethane
(D,L)-Thiorphan
(Phenylthio)acetic acid
(2-Nitrophenylthio)acetic acid
S-(Thiolauroyl)thioglycolate
disulfiram
Sodium sulfite
4-phenyl-3-butenoic acid (PBA)
tiopronin
Captopril
EDTA
Ammonium sulfite
Hydrocinnamoyl-phenylalanyl-homocysteine As mentioned above, physiological equivalents of the above PAM inhibitors are also encompassed by the invention.

In a preferred embodiment of the present invention, said expression is a heterologous protein expression.

In another preferred embodiment of the present invention, said heterologous expression takes place in a mammalian cell based expression system. Preferably, the expressed protein is at least one protein selected from the group consisting of:
an antibody, or a fragment or derivative thereof,
a fusion protein, and/or non-antibody proteins.

Preferably, the processes and media according to the present invention are suitable for the (recombinant) production of proteins comprising amino acid sequences identical to or substantially similar to all or part of one of the following proteins: an Flt3 ligand, a CD40 ligand, erythropoiesis stimulating proteins like erythropoietin (EPO), darbepoetin including darbepoetin alfa, and thrombopoietin, calcitonin, leptin, a Fas ligand, a ligand for receptor activator of NF-kappa B (RANKL), a tumour necrosis factor (TNF)-related apoptosis-inducing ligand (TRAIL), thymic stroma-derived lymphopoietin, granulocyte colony stimulating factor, granulocyte-macrophage colony stimulating factor (GM-CSF), growth factors including mast cell growth factor, stem cell growth factor, epidermal growth factor, keratinocyte growth factor, megakaryote growth and development factor, RANTES, growth hormone, insulin, insulinotropin, insulin-like growth factors, parathyroid hormone, interferons including α-interferon, β-interferon, and γ-interferon, nerve growth factor, brain-derived neurotrophic factor, synaptotagmin-like proteins (SLP 1-5), neurotrophin-3"glucagon, interleukins including IL-1, IL-la, IL-2, IL-3, IL-4, IL-5, IL-6, IL-7, IL-8, IL-9, IL-10, IL-11, IL-12, IL-13, IL-14, IL-15, IL-16, IL-17, and IL-18, colony stimulating factors, lymphotoxin-p, tumour necrosis factor (TNF), leukemia inhibitory factor, oncostatin-M, and various ligands for cell surface molecules ELK and Hek (such as the ligands for eph-related kinases or LERKS).

Further proteins that can be produced using the processes and media of the invention include proteins comprising all or part of the amino acid sequence of a receptor for any of the above-mentioned proteins, an antagonist to such a receptor of any of the above-mentioned proteins, and proteins substantially similar to such receptors or antagonists.

Also, proteins that can be produced using the methods and media of the invention include proteins comprising all or part of the amino acid sequences of differentiation antigens (referred to as CD proteins) or their ligands or proteins substantially similar to either of these. Examples of such antigens are differentiation antigens including CD20, CD22, CD27, CD30, CD39, CD40, and ligands thereto.

Enzymatically active proteins or their ligands can also be produced using the processes and media of the invention. Examples include proteins comprising all or part of one of the following proteins, or their ligands, or proteins substantially similar to one of these: metalloproteinase-disintegrin family members, kinases, glucocerebrosidase, superoxide dismutase, tissue plasminogen activator, Factor VIII, Factor IX, apolipoprotein E, apolipoprotein A-1, globins, an IL-2 antagonist, alpha-1 antitrypsin, TNF-alpha Converting Enzyme, ligands for any of the above-mentioned enzymes, and numerous other enzymes and their ligands.

The methods and media of the invention can also be used to produce chimeric proteins selected in vitro to bind to a specific target protein and modify its activity, and antibodies or portions thereof and chimeric antibodies, i.e. antibodies having human constant antibody immunoglobulin domains coupled to one or more murine variable antibody immunoglobulin domain, fragments thereof, or substantially similar proteins. The processes of the invention may also be used to produce conjugates comprising an antibody and a cytotoxic or luminescent substance. Examples of antibodies, in vitro-selected chimeric proteins, or antibody/cytotoxin or antibody/luminophore conjugates that can be produced using the methods and media of the invention include those that recognise any one or a combination of proteins including, but not limited to, any of the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1a, IL-1, IL-2, IL-3, IL-7, IL-4, IL-5, IL-8, IL-10, IL-2 receptor, IL-4 receptor, IL-6 receptor, IL-13 receptor, IL-18 receptor subunits, PDGF-β, and analogues thereof, VEGF, TGF, TGF-β2, TGF-p1, EGF receptor VEGF receptor, hepatocyte growth factor, osteoprotegerin ligand, interferon gamma, B lymphocyte stimulator, C5 complement, IgE, tumour antigen CA125, tumour antigen MUC1, PEM antigen, ErbB2/HER-2, tumour-associated epitopes that are present in elevated levels in the sera of patients, cancer-associated epitopes or proteins expressed on breast, colon, squamous cell, prostate, pancreatic, lung, and/or kidney cancer cells and/or on melanoma, glioma, or neuroblastoma cells, the necrotic core of a tumour, integrin alpha 4 beta 7, the integrin VLA-4, B2 integrins, TRAIL receptors 1,2,3, and 4, RANK, a RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, MHC I, carcinoembryonic antigen (CEA), alpha-feto-protein (AFP), tumour necrosis factor (TNF), Fc-y-1 receptor, HLA-DR 10 beta, HLA-DR antigen, L-selectin, and IFN-γ.

The processes and media of the invention can also be used to produce recombinant fusion proteins comprising any of the above-mentioned proteins or substantially similar proteins. For example, recombinant fusion proteins comprising one of the above-mentioned proteins plus a multimerisation domain, such as a leucine zipper, a coiled coil, an Fc portion of an antibody, or a substantially similar protein, can be produced using the methods and media of the invention. Specifically included among such recombinant fusion proteins are proteins in which at least a portion of TNFR or RANK is fused to an Fc portion of an antibody.

In another preferred embodiment, said mammalian cell-based expression system is at least one selected from the group consisting of:
- Baby hamster Kidney cell lines (e.g., BHK21)
- Chinese hamster ovary cell lines (e.g., CHO-K1, CHO-DG44, CHO-DXB, or CHO-dhfr⁻)
- Murine myeloma cell lines (e.g., SP2/0)
- Mouse myeloma cell lines (e.g., NSO)
- Human embryonic kidney cell lines (e.g., HEK-293)
- Human-retina-derived cell lines (e.g., PER-C6), and/or
- Amniocyte cell lines (e.g., CAP).

Preferably, hamster cell based expression system are being used. BHK21 ("Baby Hamster Kidney") cells belong to a quasi diploid established line of Syrian hamster cells, descended from a clone from an unusually rapidly growing primary culture of newborn hamster kidney tissue. Non limiting examples for BHK-21 cell lines which are commercially available and can be used in the context of the present invention are BHK-21 (C-13); BHK21-pcDNA3.1-HC; BHK570; Flp-In-BHK Cell Line; and/or BHK 21 (Clone 13) hamster cell line. Chinese hamster ovary (CHO) cells are a cell line derived from the ovary of the Chinese hamster. They are often used in biological and medical research and commercially in the production of therapeutic proteins. They were introduced in the 1960s and were originally grown as a monolayer culture. Today, CHO cells are the most commonly used mammalian hosts for industrial production of recombinant protein therapeutics and are usually grown in suspension culture.

Non limiting examples for CHO cell lines which are commercially available and can be used in the context of the present invention are FreeStyle CHO-S cells; ER-CHO Cell Line; CHO 1-15 500 CHINESE HAM; CHO-DXB, CHO-dhfr-, CHO DP-12 clone#1934; CHO-CD36; CHO-ICAM-1; CHO-K1; Ovary; HuZP3-CHOLec3.2.8.1; xrs5; CHO-K1/BB2 Cells; CHO-K1/BB3 Cells; CHO-K1/EDG8/Galpha15 Cells; CHO-K1/M5 Cells; CHO-K1/NK1 Cells; CHO-K1/NK3 Cells; CHO-K1/NMUR1 Cells; CHO-K1/NTSR1 Cells; CHO-K1/OX1 Cells; CHO-K1/PAC1/Gα15 Cells; CHO-K1/PTAFR Cells; CHO-K1/TRH1 Cells; CHO-K1/V1B Cells; 5HT1A Galpha-15-NFAT-BLA CHO-K1 Cell Line; AVPR2 CRE-BLA CHO-K1 Cell Line; CHO-S Cells SFM Adapted; DG44 Cells; Flp-In-CHO Cell Line; GeneSwitch-CHO Cell Line; NFAT-bla CHO-K1 Cell Line; T-REx-CHO Cell Line; GenoStat CHO K-1 Stable Cell Line; GenoStat CHO K-1 Stable Cell Line Kit; CHO-K1 Cell Line hamster, CHO-PEPT1 Cell line. In a particularly preferred embodiment, the hamster cell-based expression system is a CHO-dhfr-cell line.

In another preferred embodiment, said process takes place in at least one bioreactor or culture vessel selected from the group consisting of:
shake flasks
T-flasks
bags
roller bottles
bioreactors, and/or
spinner flasks.

Preferably, the said bioreactor or culture vessel can have a volume between 50 ml and 40000 l. Examples for standard bioreactor or culture vessel sizes: 50 ml (e.g. shake flask or T-flask), 500 ml, 2 l, 5 l, 15 l, 100 l and 300 l (e.g. bioreactor or bags), and 1000 l, 2000 l, 5000 l, 10000 l, 25000 l and 40000 l (large bioreactors).

In another preferred embodiment, cultivation of cells is carried out in adherent culture, for instance in monolayer culture. According to yet another preferred embodiment, the cultivation of cells may also take place in suspension culture.

Continuous and discontinuous cell culture processes can be utilized according to the present invention. Other known reactor technologies, e.g., perfusion technologies or the like, can be also utilized. Batch processes and fed-batch processes are particularly preferred embodiments.

It is particularly preferred that the PAM inhibitor serves to affect the formation of amidated amino acid residues, particularly C-terminal proline amide residues.

For most cases, it is desirable to reduce the amount of amidated amino acid residues per amino acid chain in the protein produced to <1%.

In a particularly preferred embodiment of the present invention, the PAM inhibitor is 4-phenyl-3-butenoic acid (PBA), or a physiological equivalent thereof.

PBA (also known as trans-styryl-acetic acid, or 4-PBA) is an agent which is, among others, produced by the actinomycete Streptomyces koyangensis, and which has been reported to have anti-inflammatory and antifungal effects. Furthermore, it seems to inhibit vasodilatation.

In the present context, PBA seems to inhibit the cleavage of the C-terminal glycine residue, i.e., it is an inhibitor of the Peptidylglycine alpha-hydroxylating monooxygenase (PHM), which is one enzyme of the PAM complex.

Quite surprisingly, the inventors of the present invention have for the first time shown that a PAM inhibitor, e.g., 4-phenyl-3-butenoic acid (PBA), can be used, alone or in combination with one or more other agents, in a cell culture process, a protein expression process, a cell culture medium and/or a protein expression medium, to control and/or adjust the amount of amidated amino acid residues, particularly C-terminal proline amide, in a dose dependent manner. Data supporting these findings are disclosed herein, e.g., under FIG. 1, FIG. 2 and FIG. 3 and respective descriptions.

Preferably, 4-phenyl-3-butenoic acid (PBA), or a physiological equivalent thereof, is used in a concentration of $\geq 0.01$ μM and $\leq 300$ μM ($=$μMol l$^{-1}$). More preferably, said concentration range is between $\geq 5$ μM and $\leq 200$ μM, even more preferably between $\geq 10$ μM and $\leq 150$ μM, and most preferably between $\geq 45$ μM and $\leq 110$ μM. For other PAM inhibitors, or their physiological equivalents, other concentration ranges may apply.

It should be noted that in the feed solution (also called "shot solution"), the concentration can be significantly higher than in a cell culture medium, or in a cell culture fluid, e.g, up to 3 M ($=$Mol l$^{-1}$).

When compared to cell mass, 4-phenyl-3-butenoic acid (PBA), or a physiological equivalent thereof, can be used in a concentration of $\geq 0.01$ mmol/kg of cell mass and $\leq 1$ mmol/kg of cell mass. More preferably, said concentration range is between $\geq 0.03$ mmol/kg of cell mass and $\leq 0.5$ mmol/kg of cell mass.

It should be noted that in the feed solution (also called "shot solution"), the concentration can be significantly higher than in a cell culture medium, or in a cell culture fluid, namely between $\geq 0.1$ and $\leq 10$ mmol/kg feed solution, preferably $\geq 0.4$ and $\leq 5$ mmol/kg feed solution.

The following table shows how PBA was applied experimentally in the production of five different therapeutic proteins.

| | PBA concentration | | | |
|---|---|---|---|---|
| Protein | when fermentation starts [mmol/kg cell mass] | in shot solution [mmol/kg shot solution] | amount of shot solution applied | application mode of shot solution |
| 1 | 0.066 | 0.440 | 200 kg/shot, 5 shots | first shot when viable cell density was 4.0E+06, but at least 84 hrs after start of fermentation, then 24, 48, 72, and 96 hrs +/− 2 hrs after first application |
| 2 | 0.050 | 0 | 0 | n.a. |
| 3 | 0.042 | 0.626 | 40 kg/shot, 8 shots | first shot when viable cell density was 5.4-7.0E+06, then daily until day 10 + day 12 |
| 4 | 0 | 4.994 | 1 shot of 25 kg 5 shots of 5 kg | 1st shot prior to Inoculation, shots 2-6 on days 4, 6, 8, 10 and 12 |

-continued

| Protein | PBA concentration when fermentation starts [mmol/kg cell mass] | in shot solution [mmol/kg shot solution] | amount of shot solution applied | application mode of shot solution |
|---|---|---|---|---|
| 5 | 0 | 4.994 | 1 shot of 37.5 kg<br>5 shots of 15 kg | 1.5% of final working volume on day 0 and 0.6% of final wv on days 4, 6, 8, 10 and 12 |

The PAM inhibitor, or its physiological equivalent, can be added to the medium at the start of the cell culture process. Alternatively, the PAM inhibitor, or its physiological equivalent, can be supplemented during the cell culture process, e.g., as ingredient of a feed medium (also called "feed solution" or "shot solution").

The proteins obtained from such cell culture process can be used for the preparation of pharmaceutical preparations. In addition, the proteins obtained from such cell culture process can be administered together with other components of biologically active agents such as pharmaceutically acceptable surfactants, recipients, carriers, diluents and vehicles.

Definitions

The term "PAM inhibitor", as used herein, relates to an agent that lowers the rate of catalysis of the PAM enzyme complex. Said PAM inhibitor can thus either affect the PAM enzyme complex as such, or affect Peptidylglycine alpha-hydroxylating monooxygenase (PHM), which is responsible for cleaving a C-terminal glycine residue, or peptidylamidoglycolate lyase (PAL), which is responsible for the actual amidation reaction.

As used herein, the term "physiological equivalent of a PAM inhibitor" relates to chemical PAM inhibitor derivatives, which have, in a physiological setting (e.g., a cell culture fluid), the same potential effect as the said PAM inhibitors. Said equivalents are, for example, salts or esters (whenever chemically adequate) of the said PAM inhibitors, which dissolve, or are hydrolyzed by ubiquitous esterases, in the medium to form the actual PAM inhibitor.

The term "pharmaceutical preparation", as used herein, indicates a composition suitable for or adapted to administration to a mammal, especially a human.

As regards the term "fusion protein", which is used herein synonymously with the term "fusion peptide", proteins are meant which are created through the joining of two or more genes which originally coded for separate proteins. Translation of this fusion gene results in a single polypeptide with functional properties derived from each of the original proteins. The meaning of this term encompasses chimeric and humanized antibodies, as well as constructs consisting, e.g., of a receptor domain and an IgG Fc segment As used herein, the terms "heterologous protein expression" and "heterologous protein" refers to both proteins and peptides which are not naturally produced by the expression system, e.g. the host cell. The latter has to be genetically modified in order to express said heterologous protein.

As used herein, the term "antibody" refers to monoclonal antibodies (mAbs), multispecific antibodies, human antibodies, humanized antibodies, synthetic antibodies, chimeric antibodies, polyclonal antibodies, camelized antibodies, single-chain Fvs (scFv), single chain antibodies, immunologically active antibody fragments (e.g., antibody fragments capable of binding to an epitope, e.g., Fab fragments, Fab' fragments, F(ab')$_2$ fragments, Fv fragments, fragments containing either a VL or VH domain or a complementary determining region (CDR) that immunospecifically binds an antigen, etc.), bi-functional or multi-functional antibodies, disulfide-linked bispecific Fvs (sdFv), intrabodies, and diabodies, and epitope-binding fragments of any of the above. In particular, the term "antibody" is intended to encompass immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG$_1$, IgG$_2$, IgG$_3$, IgG$_4$, IgAi and IgA$_2$) or subclass.

As used herein, the term "non-antibody proteins" relates to physiologically active proteins which are not antibodies. Such definition encompasses, among others, insulin, somatropin, erythropoietin, interferon alpha or G-CSF, tissue plasminogen activator (tPA), factor VIII, and/or interleukin 2, or fragments or derivatives thereof.

As used herein, the term "fragment of an antibody" shall refer to fragments of such antibody retaining, in some cases, particular antibody properties, e.g., target binding capacities. Examples for such fragments are:
  a CDR (complementarity determining region)
  a hypervariable region,
  a variable domain (Fv)
  an IgG heavy chain (consisting of VH, CHL hinge, CH2 and CH3 regions)
  an IgG light chain (consisting of VL and CL regions), and/or
  a Fab and/or F(ab)2.

As used herein, the term "derivative of an antibody" shall refer to protein constructs being structurally different from, but still having some structural relationship to, and retaining some functional property of, the common antibody concept, e.g. scFv, as well as bi-, tri- or higher specific antibody constructs, pegylated antibody constructs and the like.

Similar concepts apply to "fragments or derivatives of a protein" in the meaning of the present invention.

As used herein, the term "cell culture medium" shall refer to all kinds of media which are used in the context of culturing cells. Typically, a cell culture medium comprises amino acids, at least one carbohydrate as an energy source, trace elements, vitamins, salts and possibly additional components (e.g. in order to influence cell growth and/or productivity and/or product quality).

As used herein, the terms "feed", "feed medium" or "feed solution" refer to a kind of cell culture medium or to a solution of specific components, which is added as supplement to a cell culture during the process usually in order to influence cell growth and/or productivity and/or product quality.

As used herein, the term "cell culture fluid" shall refer to the actual liquid in which the cells are being cultured. This means that said fluid can contain, in contrast to a cell culture medium or feed according to the above definition, metabolites produced by the cells, cell debris, cellular proteins (e.g. enzymes, or recombinant protein) and/or degradation products of the said PAM inhibitors, and can furthermore be reduced in its nutrient content.

As used herein, the term "amount of amidated amino acid residues" relates to amidated amino acid residues formed during or after protein expression at the C-terminus of the protein. This relates, specifically, to the amount of amidated proline. Under certain circumstances, proline residues in a protein can be amidated post-translationally, leading to the formation of, e.g., proline amide (Pro-$NH_2$). This is unwanted in some cases, e.g. when the amount of proline amide in the protein which is to be produced is higher, or lower, than in a reference protein.

Prolin amidation effected by the PAM enzyme complex relies basically on the hydrolysis and oxidation of a C-terminal peptide bond between Pro and R of a translated protein, in which R can be one or more than one amino acid residue, for example, Gly, Leu, Ile, Val, or Phe, or Gly-Lys. The reaction is in most cases catalyzed by the PAM enzyme complex (see above). Depending on the expression host and the protein expression conditions, the share of translated proteins carrying at least one post-translational Pro-$NH_2$ can be in the range of $\geq 0$ -$\leq 100\%$. The said amidation leads to an elevation of protein pH and is thus a basic variant.

In monoclonal antibodies or their derivatives, proline amide (PA) is typically created by post-translational removal of C-terminal lysine and glycine and amidation of the now C-terminal proline residue, e.g. at the heavy chains of the protein.

Proline amidation is of importance for the function of various proteins, e.g. Calcitonin. Its function in mAbs is so far not known.

The amount of proline amide can be identified and quantified by various analytical methods, by distinguishing the amidated variant from the non-amidated one by physico-chemical differences such as charge, hydrophobicity or mass. The most common method is ion exchange chromatography, as the CEX-CPB method (cation exchange chromatography after digestion by carboxypeptidase B), exploiting the charge alteration due to proline amidation. For antibodies, co-elution of proline amide variants with lysine variants is avoided by removal of lysine residues using carboxypeptidase B digestion prior to chromatographic separation. Additional co-elution with other basic variants, however, can result in a quantification background of several percent (e.g. 4%). Proline amide variants plus background are termed "Pseudo 1K" for eluting at the chromatographic position of the antibody variant with one C-terminal lysine residue. "Pseudo 2K" encompasses the proline variants plus background eluting at the chromatographic position of the antibody variant with two C-terminal lysine residue. The difference to the CEX method (i.e. CEX without lysine removal by CPB digestion) is indicating the amount of antibody variants with lysine residues, termed "Real 1K" and "Real 2K". The quantification by CEX (-CPB) returns the percentage of proline amidated antibodies relative to all antibody molecules in a solution. An analytical test method which unambiguously can identify and quantify amidated proline variants is RP-HPLC (reversed-phase high-performance-liquid-chromatography) of endopeptidase (e.g. LysC, Trypsin) digested protein, so called peptide mapping, using UV (ultraviolet) or MS (mass-spec) detection. The quantification by RP-HPLC peptide mapping returns for an antibody the percentage of proline amidated heavy chains relative to all heavy chains.

"Pseudo 1K" is the variant determined by CEX-CPB where one of the two heavy chains of an antibody (IgG) has a proline amide at its C-terminus. "Pseudo 2K" is the variant determined by CEX-CPB where both heavy chains of a monoclonal antibody have a proline amide at their C-termini.

As used herein, the term "concentration" of a given agent relates to a concentration in a cell culture medium (e.-g. cell culture medium, or feed medium, or feed solution), or in a cell culture fluid.

Disclaimer

To provide a comprehensive disclosure without unduly lengthening the specification, the applicant hereby incorporates by reference each of the patents and patent applications referenced above.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

Brief Description of the Examples and Drawings

Additional details, features, characteristics and advantages of the object of the invention are disclosed in the subclaims, and the following description of the respective figures and examples, which, in an exemplary fashion, show preferred embodiments of the present invention. However, these drawings should by no means be understood as to limit the scope of the invention.

Experiments: Effect of PAM Inhibitors on Amino Acid Amidation/Profile Amid Formation In their experiments, the inventors focused on published PAM inhibitors as potential medium components. Among the screened components are, i.e., sodium sulfite, tiopronin, captopril, EDTA, ammonium sulfite, L-histidine, D-histidine, ammonium meta thiomolybdate, L-carnosine, penicillamine, 4-phenyl-3 butenoic acid (PBA).

Two recombinant proteins were used to investigate the effect of PAM inhibitors on amino acid amidation/proline amid formation, i.e., a monoclonal antibody (human-mouse-chimeric IgG), and an Fc-fusion protein. CHO cells were used as expression system.

PBA was shown to have the strongest effect on proline amide formation, while not impacting growth or other product quality attributes significantly.

Based on these results, the inventors concluded that the composition of a cell culture medium can be adapted by addition of PBA (e.g., 100 µM). In another approach, PBA can be supplemented to the medium as well as to a feed solution. For example, the culture can be started without, or with low amounts of, PBA, and increasing amounts of PBA can be added after the cell culture has reached its peak cell densities, but before the main amount of recombinant protein is being produced. This may support higher peak cell densities and higher product titers at harvest compared to having the final amount of PBA already present during the growth phase.

DRAWINGS

FIG. 1: Influence of PAM inhibitors on proline amide (PA) formation, quantified as 'pseudo 1K' in CEX-CPB analysis, on a monoclonal antibody (chimeric IgG) expressed in CHO cells. PBA was shown to have the strongest effect on proline amide formation when supplemented to the cell culture, with concentrations of 10 μM or 100 μM in the cell culture medium decreased the amount of pseudo 1K from app. 10% to app. 8%, or app. 5%, respectively. 5% pseudo 1K in CEX-CPB corresponds to 0-2% proline amide per heavy chain as confirmed by peptide mapping.

Figure 2:
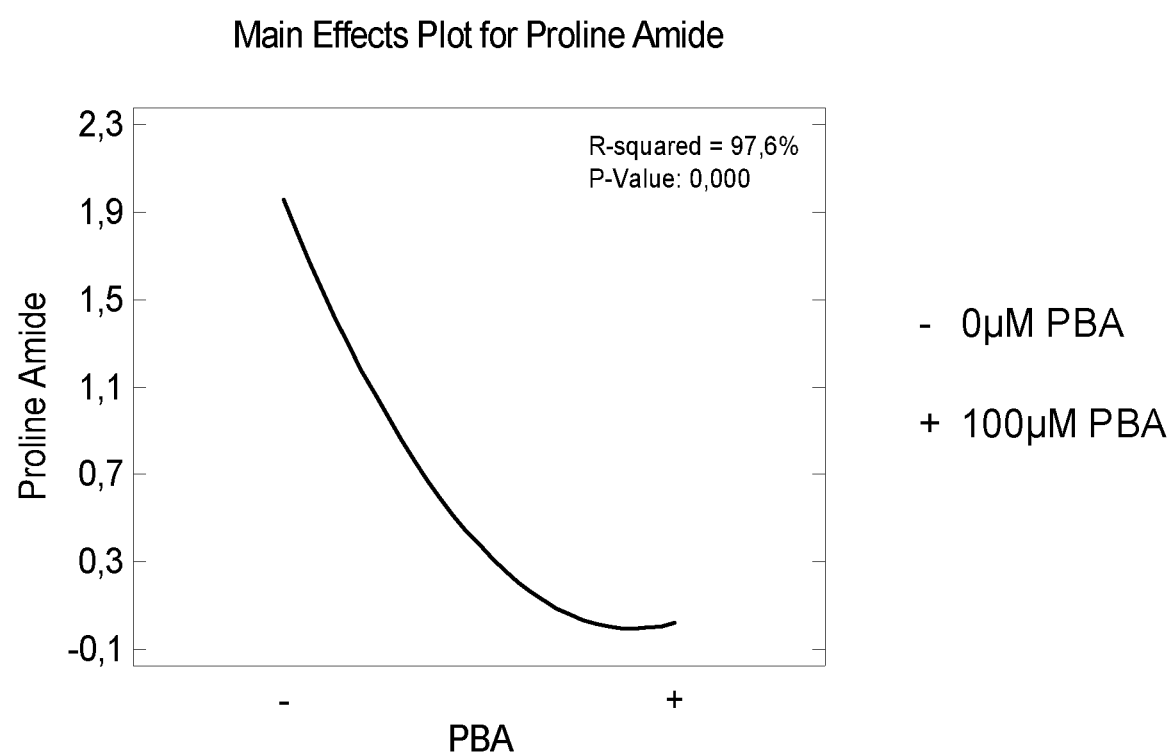

FIG. 2: Influence of PAM inhibitor PBA on proline amide formation on an Fc-fusion protein expressed in CHO cells, as quantified by peptide mapping. Supplementing the cultures of recombinant CHO cells with various concentrations of PBA up to 100 μM decreased the amount of proline amide (% per heavy chain) in a dose-dependent effect curve from app. 2% (no PBA) to app. 0.1% (100 μM PBA).

Figure 3:
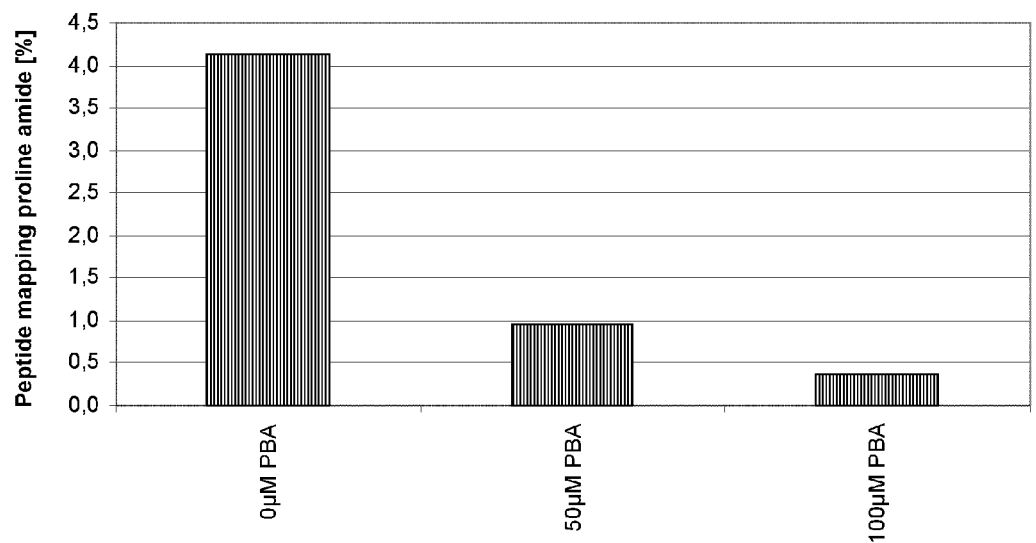

FIG. 3: Influence of PAM inhibitor PBA on proline amide formation on an Fc-fusion protein expressed in CHO cells, as quantified by peptide mapping. Supplementing the culture of recombinant CHO cells with 50 μM or 100 μM PBA resulted in a decrease of proline amide (% per heavy chain) from >4% to <1% and <0.5% respectively.

REFERENCES

Chew, G: Substrate-Based Inhibitors of Peptidylglycine Amidating Monooxygenase (PAM) as Anti-Proliferative Drugs for Cancer. Master Thesis (University of South Florida), 2003

Bauer et al (2007): Anti-Inflammatory Effects of 4-Phenyl-3-butenoic Acid and 5-(Acetylamino)-4-oxo-6-phenyl-2-hexenoic Acid Methyl Ester, Potential Inhibitors of Neuropeptide Bioactivation J Pharmacol Exp Ther March 2007 320:1171-1177

What is claimed is:

1. A cell culture medium for the heterologous expression of a protein, which medium comprises a feed, and which medium further comprises a PAM inhibitor, or a physiological equivalent thereof.

2. A process for the heterologous expression of a protein, comprising culturing one or more cells in a cell culture medium, wherein said cell culture medium comprises a PAM inhibitor, or a physiological equivalent thereof, and wherein said one or more cells expresses a heterologous protein.

3. The cell culture medium according to claim 1, wherein the heterologous expression takes place in a mammalian cell based expression system.

4. The cell culture medium according to claim 1, wherein said protein is at least one protein selected from the group consisting of:

an antibody or a fragment or derivative thereof,
a fusion protein, and
a physiologically active non-antibody protein.

5. The cell culture medium according to claim 3, wherein said mammalian cell-based expression system is at least one selected from the group consisting of:

Baby hamster Kidney cell lines (BHK21),
Chinese hamster ovary cell lines (CHO-K1, CHO-DG44, CHO-DXB, or CHO-dhfr⁻),
Murine myeloma cell lines (SP2/0),
Mouse myeloma cell lines (NS0),
Human embryonic kidney cell lines (HEK-293),
Human-retina-derived cell lines (PER-C6), and
Amniocyte cell lines (CAP).

6. The process according to claim 2, wherein said process takes place in at least one bioreactor or culture vessel, wherein the at least one bioreactor or culture vessel is selected from the group consisting of: a shake flask, a T-flask, a roller bottle, a bag, a bioreactor, and a spinner flask.

7. The cell culture medium according to claim 1, wherein the PAM inhibitor is 4-phenyl-3-butenoic acid (PBA), or a physiological equivalent thereof.

8. The cell culture medium according to claim 7, wherein 4-phenyl-3-butenoic acid (PBA), or a physiological equivalent thereof, is used in a concentration of ≥0.01 μM and ≤3M.

9. The process according to claim 2, wherein the heterologous expression takes place in a mammalian cell based expression system.

10. The process according to claim 2, wherein said protein is at least one protein selected from the group consisting of: an antibody or a fragment or derivative thereof, a fusion protein, and a physiologically active non-antibody protein.

11. The process according to claim 9, wherein said mammalian cell based expression system is at least one selected from the group consisting of:

Baby hamster Kidney cell lines (BHK21),
Chinese hamster ovary cell lines (CHO-K1, CHO-DG44, CHO-DXB, or CHO-dhfr⁻),
Murine myeloma cell lines (SP2/0),
Mouse myeloma cell lines (NS0),
Human embryonic kidney cell lines (HEK-293),
Human-retina-derived cell lines (PER-C6), and
Amniocyte cell lines (CAP).

12. The process according to claim 2, wherein the PAM inhibitor is 4-phenyl-3-butenoic acid (PBA), or a physiological equivalent thereof.

13. The process according to claim 12, wherein 4-phenyl-3-butenoic acid (PBA), or a physiological equivalent thereof, is used in a concentration of ≥0.01 μM and ≤3M.

* * * * *